United States Patent [19]

Davis

[11] 4,138,892

[45] Feb. 13, 1979

[54] ELECTRICALLY HEATED MOLD FOR MAKING TEST SPECIMENS OF CONCRETE

[76] Inventor: George B. Davis, P.O. Box 1096, Boulder, Colo. 80302

[21] Appl. No.: 808,881

[22] Filed: Jun. 22, 1977

[51] Int. Cl.² .................. B41B 11/54; G01N 25/02
[52] U.S. Cl. ........................ 73/432 SD; 73/15 R; 249/170; 249/DIG. 4
[58] Field of Search .............. 249/78, 170, DIG. 4; 73/432, 15 R

[56] References Cited

U.S. PATENT DOCUMENTS

| 166,667 | 8/1875 | Watkins | 249/170 |
|---|---|---|---|
| 1,533,341 | 4/1925 | Rodler | 249/170 |
| 1,789,883 | 1/1931 | Roth | 249/78 |
| 2,392,561 | 1/1946 | Weber | 249/170 |
| 3,421,184 | 1/1969 | Ford et al. | 249/170 |
| 3,860,062 | 1/1975 | McMurray | 249/78 |

*Primary Examiner*—Herbert Goldstein
*Attorney, Agent, or Firm*—Burton and Dorr

[57] ABSTRACT

An electrically heated mold for making test specimens of concrete. The mold has two substantially identical mold halves pivotally mounted to each other and electric heating units selectively operated in response to the temperature variations in the concrete of the main structure. Each mold half has a heat transferring wall member which has a mold surface and an outer surface against which one of the heating units is placed. The mold is insulated and has a number of additional features designed to facilitate manufacture and operation of the mold as well as to increase its working life. These features include aligning members for aligning the halves of the mold as they close, two symmetrically positioned securing members that can be manipulated simultaneously by one person, an arrangement for preventing material from passing between the mold halves as they open in order to protect the insulation adjacent that area, an arrangement for initially prying the mold halves apart, and a stripping shoe for removing any molded test specimen that becomes stuck to one of the mold halves. The stripping shoe removes the molded test specimen without damaging the boundary areas and edges necessary for proper testing of the specimen.

34 Claims, 15 Drawing Figures

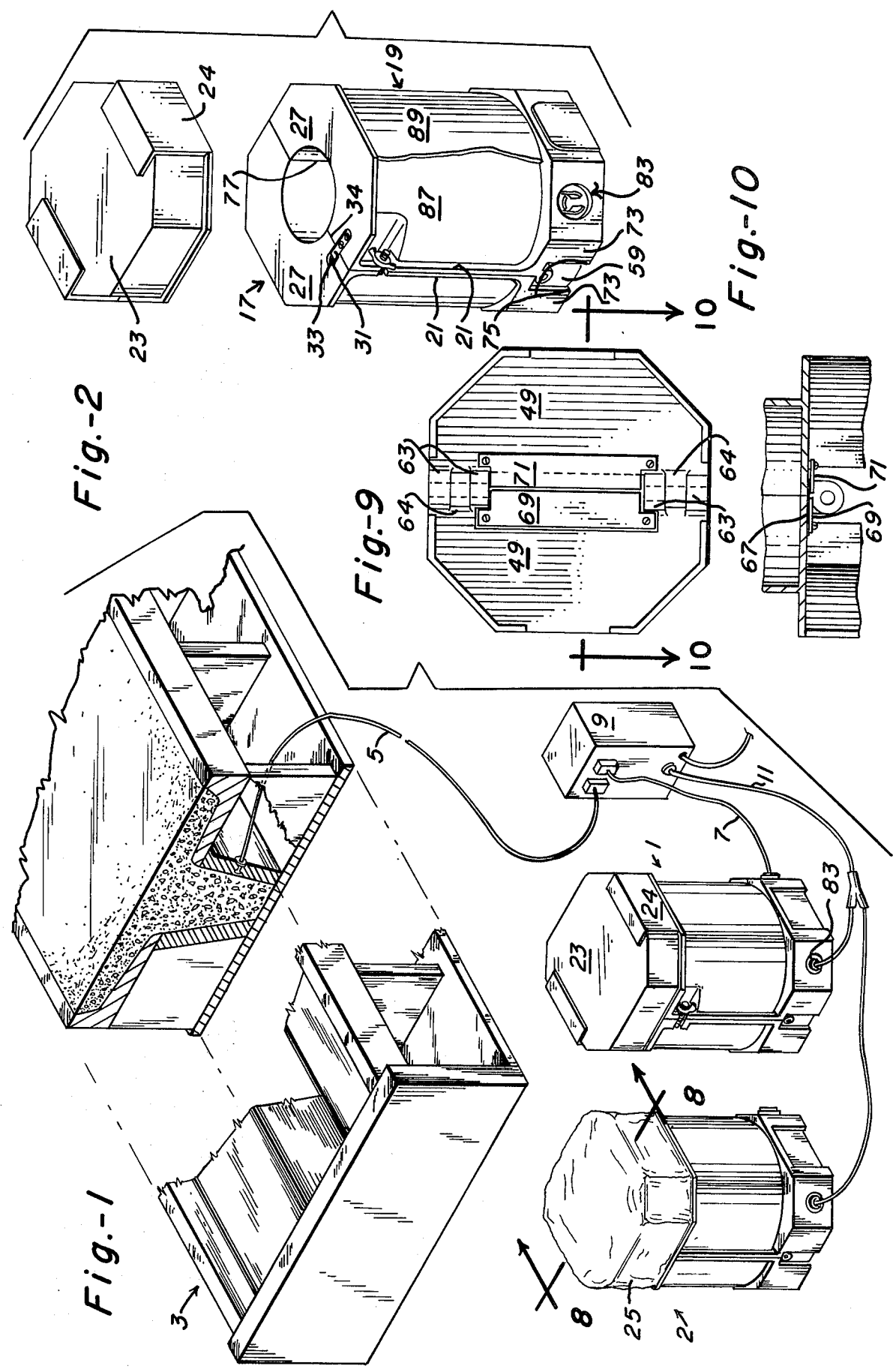

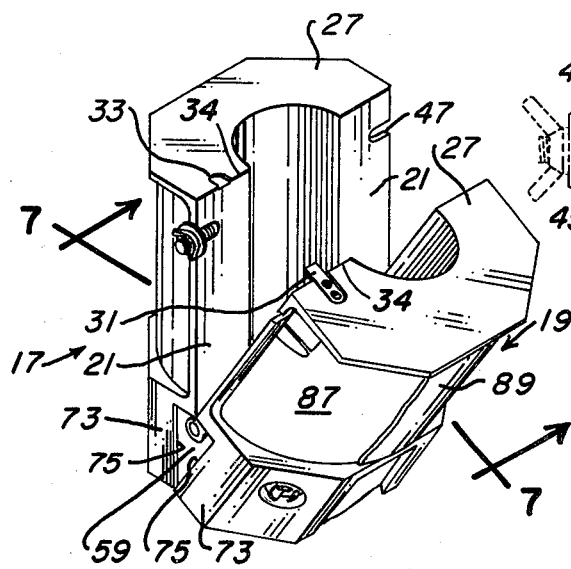
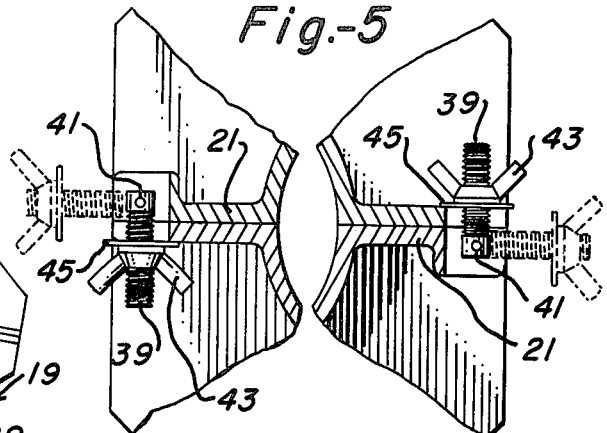
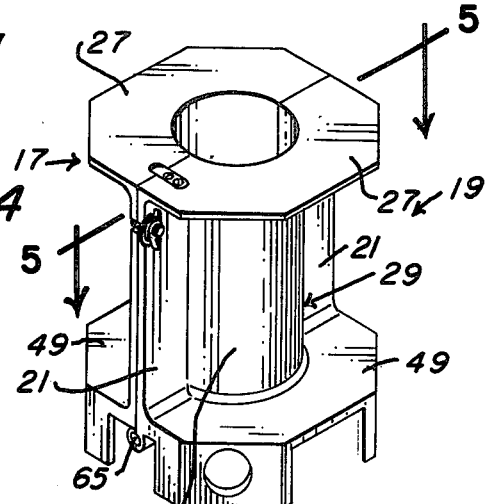
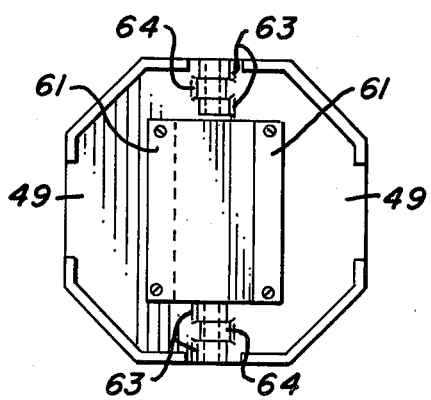
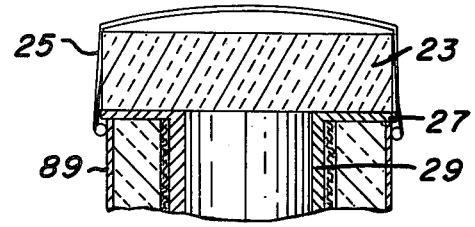
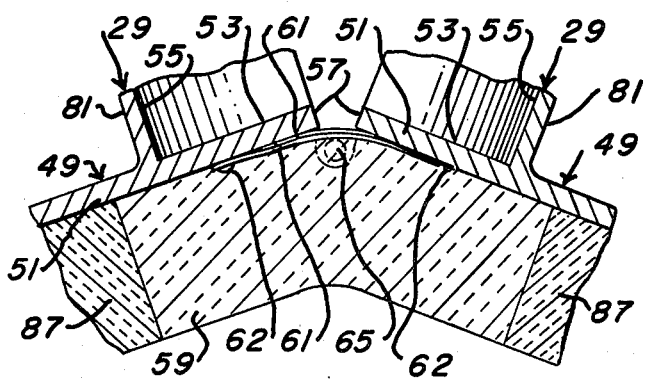

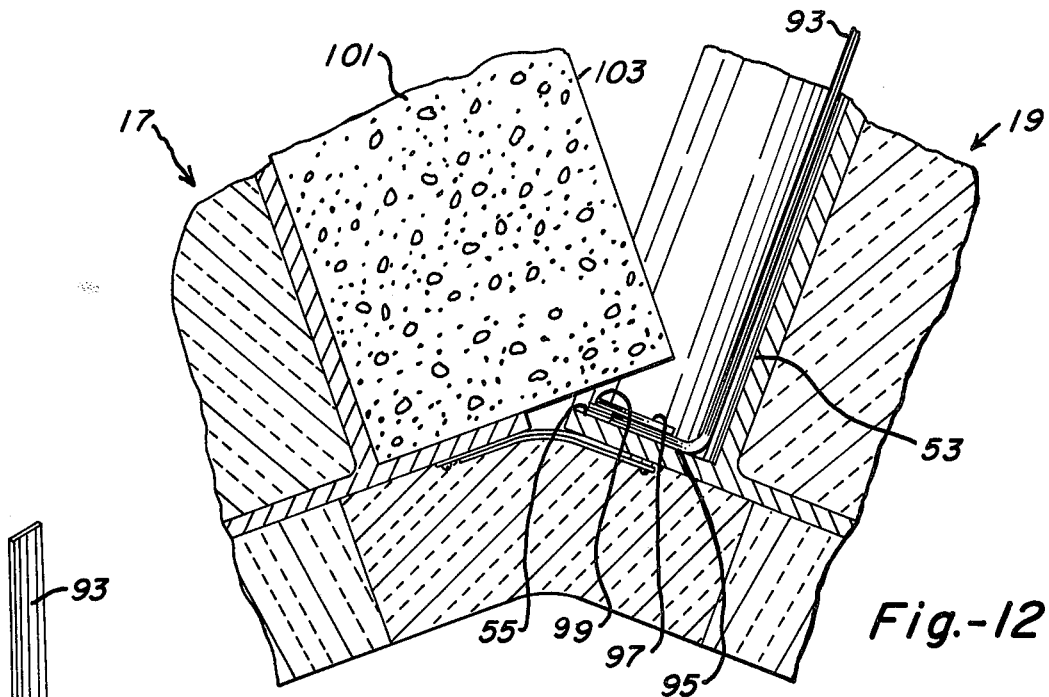
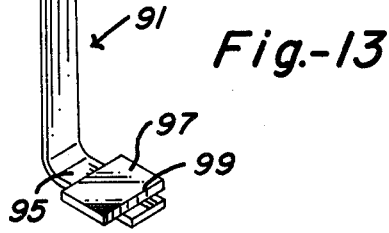
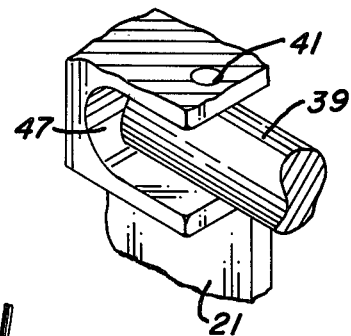
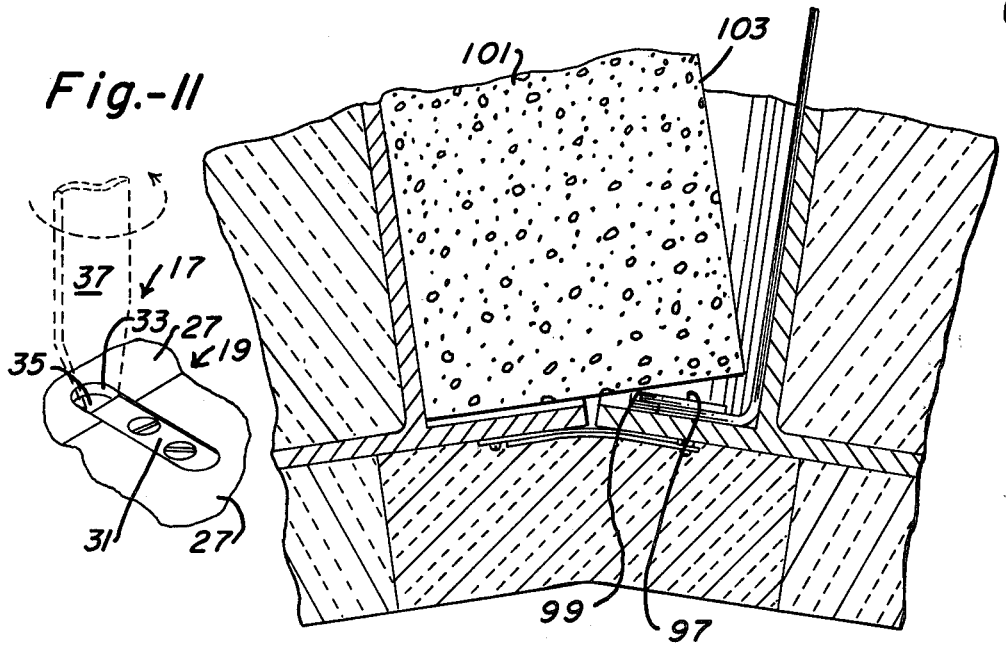

ELECTRICALLY HEATED MOLD FOR MAKING TEST SPECIMENS OF CONCRETE

FIELD OF THE INVENTION

This invention relates to the field of molds for making test specimens and more particularly to the field of molds for making cylindrical test specimens of concrete.

BACKGROUND OF THE INVENTION

The making of accurate test specimens is essential to the construction industry. Ideally, the test specimen would have the identical properties of the main structure so that results of tests performed on the specimen could be attributed directly to the main structure or extrapolated by known formulas to accurately predict the properties of the main structure. In practice, the attainment of identical properties is extremely difficult especially if the volume difference between the main structure and the test specimen is large. In the construction industry, this volume difference is usually extremely large.

Concrete is a widely used material in the construction industry and there are a number of factors that affect its ultimate strength. Some of these factors are mechanical such as the materials used, the mix proportions, and the extent to which the concrete is compacted and some of these factors are chemical such as the time-temperature curve of the curing process. The reaction of the concrete mixture is itself exothermic and it is the practice in many fields of the concrete industry to accelerate the curing process by heating the skins of the forms. Normal curing usually has a time-temperature curve that is relatively flat during the initial pre-set hours and then rises for a few hours. If the mold is insulated, this rise can be on the order of 30° F. above the pouring temperature. With accelerated curing, heat is added to the concrete in the form to reduce the overall time of the curing process. This practice is particularly common in making pre-cast and pre-formed concrete. In one such process, live steam, hot water, hot oil, or other hot fluid is passed through a system of pipes positioned near the skin of the form. The skin of the form is then actually heated by energy radiating from the pipes. A less common procedure is to place an electric heating unit against the skin of the form. In these accelerated curing procedures, the temperature of the concrete in the form is raised after the initial pre-set period of 1-3 hours up to 135°-160° F. in 2-3 hours (20°-40° per hour) and maintained at the elevated temperature for about 8 hours. In accelerated curing and normal curing, a vapor shield is usually placed about the form so that the concrete will not dehydrate.

In making test specimens, accurately duplicating the time-temperature curve of the curing process of the main structure is as important, if not more important, than accurately duplicating the materials, mix, compaction, and other mechanical features. One technique for trying to match the two curves when the main structure is curing without the addition of external heat is to place the mold for the test specimen as near to the main structure as possible. This procedure for making test specimens has proven to be most unsatisfactory regardless of how close the two are placed and regardless of whether the main structure and mold are insulated or not. One problem with this procedure is that the ratio of the volume of the test material to the surface area of the mold is much smaller than the ratio of the volume of the main structure to the surface area of its form. Consequently, the mold affects the temperature of the specimen much more than the form affects the temperature of the main structure. Further, the mold is often constructed from a different material than that of the form so that the heat transferring properties are different. Due to these factors and other factors, the time-temperature curve of the test specimen in the mold is often much different from that of the main structure. In practice, it has become necessary in many cases to add external heat to the mold of the test specimen in order for it to match the temperature created in the main structure, expecially if the main structure is insulated. If the curing of the main structure is accelerated, it is mandatory that the test specimen also be externally heated.

One known manner of substantially matching the time-temperature of a main structure is to place the test specimen and molds in a liquid whose temperature is controlled according to the temperature of the main structure as disclosed in the British Pat. No. 1,300,099 to Thompson issued on Dec. 20, 1972. This technique has several drawbacks. One disadvantage of Thompson's system is that it is bulky and would be difficult to work with in the field. Another disadvantage is that Thompson senses the water temperature around the molds rather than the temperature of the test specimen itself or the temperature of the mold's surface immediately adjacent the test specimen. He also heats the water which heats the mold rather than heating the mold directly. Thompson's heat must pass from the water through the mold to the test specimen. Since Thompson adds his heat to the water and controls this addition of heat by monitoring the temperature of the water, he has the further problem of uniformly delivering the heat to the molds without the establishment of convection currents and temperature gradients in the water that would affect the accurate delivery of heat to his molds and the accurate reading of the water temperature. This problem is particularly acute if the water volume is relatively large.

Apart from the problem of accurately heating the test specimen within the mold, the mold itself should have certain characteristics of its own. It should be easily formed or cast, long-lasting, and easy to operate. For ease of forming or casting, it is best to have a mold whose halves are substantially identical so that they themselves can be made from the same mold. To be long-lasting, the mold should be strong without being unduly heavy and have as few moving parts as possible as well as features to protect the areas most vulnerable to wear and abuse. For ease of operation, the mold should also have as few as possible moving parts that must be manipulated during the molding process. Further, the halves of the mold should be able to be quickly aligned as the mold closes and to be quickly and easily screwed together. The mold should also have an arrangement for initially prying the halves apart to remove the test specimen, an arrangement for stopping the movement of the mold halves relative to each other at a pre-determined open position, and an arrangement for removing a test specimen that may become fixed to the mold surface of one of the mold halves. This arrangement for removing or stripping a test specimen from fixed engagement with one of the mold halves should do so without disturbing the boundary areas including their edges that are necessary for proper testing of the specimen. In this regard, the symmetry of the mold halves is also desirable to avoid localized stressing of the test specimen and damage to the boundary areas as the mold is opened. In addition to these characteristics of the mold, the mold must be water tight if it is to meet ASTM standards.

Numerous U.S. Patents illustrate molds, however, none of these is known to have the symmetry, ease of operation, or durability of the present invention. Examples of molds whose halves are pivotally mounted to each other include U.S. Pat. No. 166,667 to Watkins issued on Aug. 10, 1875, U.S. Pat. No. 1,739,769 to Redmann issued on Dec. 12, 1929 and U.S. Pat. No. 1,927,717 issued to Rothmann on Sept. 19, 1933. Among other things, these patents lack symmetry and ease of production and operation. Watkins, for example, has an asymmetric pivot arrangement as well as asymmetrically positioned securing means. U.S. Pat. No. 1,533,341 to Rodler issued on Apr. 14, 1925 illustrates a mold with aligning pins 11 for the mold halves and securing members 7-10. Rodler's mold halves 1 and 2 are not pivotally mounted to each other and he has no means for initially prying the mold apart. U.S. Pat. No. 2,986,797 to Aisenberg issued on June 6, 1971 also shows the use of aligning pins 36 which are located between the ends of the mold halves like those of Rodler. U.S. Pat. No. 3,454,257 to Dupuis issued on July 8, 1969 and U.S. Pat. No. 2,974,385 to Leisenring issued on Mar. 14, 1971 illustrate asymmetric molds which are opened and closed from only one side. Such molds have the problem of losing their symmetry after numerous uses as well as during use (see lines 33-44 of Dupuis' column 3). Such molds also have the problem of stressing the test specimen and perhaps scarring the boundary areas of the specimen when the mold is opened. Their lack of symmetry also makes them somewhat difficult to operate quickly. An example of a mold whose halves are mounted for sliding movement relative to each other is illustrated in U.S. Pat. No. 812,935 to Knapp issued on Feb. 20, 1906.

The ideal mold for making test specimens of concrete or other material would be easy to make, durable, easy to operate, and able to accurately follow the temperature variations in the main structure. The present invention offers such a mold.

SUMMARY OF THE INVENTION

This invention involves an electrically heated mold for making test specimens of concrete or other material. The mold has substantially identical mold halves which are pivotally mounted to each other. Each mold half has a thin, heat transferring wall member with two sides. A heating unit is positioned adjacent the surface of one side and the other side of each wall member forms a recessed mold surface. A floor member with a mold surface is attached to each wall member. When the mold is closed, the floor member and wall member of one mold half abut the corresponding members of the other mold half along edges to form an open-ended mold shape into which concrete can be poured. An insulated top member can be placed over the open end of the mold shape and held in place by a waterproof cap.

The mold has a layer of insulation about the heating units and the floor members. The power to the heating units is controlled by a control means which has thermocouples monitoring the temperature of the concrete in the main structure and in the mold. The control means compares the two readings from the thermocouples and adjusts the power to the heating units accordingly so that the time-temperature curve of the concrete in the mold matches that of the concrete in the main structure. In one embodiment, each wall member has a passage extending between the opposing sides into which one thermocouple is placed. The mold halves also have flanges extending outwardly of each wall member beyond the insulating layer for passing any excess heat outwardly of the mold.

The invention includes a number of features designed to facilitate the making and operation of the mold as well as to increase its working life. In one embodiment, two thin sheets of spring steel are placed in an overlapping relationship immediately below the floor members of the mold to prevent material from passing between the edges of the floor members as the mold is opened. This protects the insulation material located below the floor members. In another embodiment, a single sheet of spring steel is positioned between the floor members to protect the insulation. The invention also has an arrangement for aligning the mold halves as the mold closes and an arrangement for initially prying the mold open after the specimen has been made. The mold has two securing members for selectively holding the mold halves together. These securing members are pivotally mounted to each respective mold half and can be easily and quickly operated to secure the mold halves to each other. The securing members are positioned approximately 180° from each other about the mold and extend in opposite directions so that they can be simultaneously manipulated by one person.

The invention further includes stop members symmetrically positioned on each mold half adjacent to the pivotal axis. The insulation near the pivot arrangement is flexible to accommodate the movement of the halves and the stop members of one mold half abut corresponding members on the other mold half to prevent the mold from opening past a predetermined position. The invention also includes flanges extending outwardly from the wall members adjacent the open end of the mold shape. These flanges serve as working surfaces and protection for the other parts of the mold. A thin, protective cover can also be placed about all of the insulating portions of the mold to protect them from wear and abuse. Another feature of the invention is a stripping shoe that can be used to remove a test specimen that has become stuck to a mold half. The stripping shoe will remove the test specimen without damaging the boundary areas and edges necessary for proper testing of the specimen.

OBJECTS OF THE INVENTION

It is an object of this invention to provide a new and novel electrically heated mold for making concrete test specimens.

It is also an object of this invention to provide a new and novel electrically heated mold for making test specimens of a material being used in a main structure, which mold can accurately follow the temperature variations in the main structure.

Another object of the invention is to provide a new and novel mold which is easy to make and operate as well as being durable.

It is also an object of the invention to provide a new and novel mold design which has substantially identical mold halves to facilitate manufacture and use.

Another object of the invention is to provide a new and novel mold with securing members symmetrically attached to each mold half and extending in opposite directions for quick and easy manipulation by one person.

Another object of the invention is to provide a new and novel mold which has flanges for dissipating excess heat outwardly of the mold and protecting portions of the mold from wear and abuse. Two of these flanges also serve to provide a working surface near the open end of the mold shape.

Another object of the invention is to provide a mold with superior insulating properties. A portion of the insulation is flexible to accommodate the pivotal movement of mold halves.

It is also an object of this invention to provide a new and novel mold which has flexible sheet members positioned adjacent the pivot arrangement of the mold for preventing any material that might be chipped off the test specimen from contacting and damaging the insulation positioned near the pivot arrangement.

It is an object of this invention to provide a new and novel mold which has stop members for preventing the mold halves from opening past a predetermined position.

Another object of this invention is to provide a new and novel mold which has an arrangement for aligning the mold halves as they are closed.

It is also an object of this invention to provide a new and novel mold which has an arrangement for prying open the mold halves.

Another object of this invention is to provide a stripping shoe for use with the mold for removing a test specimen that has become stuck to one of the mold halves without damaging the boundary areas and edges necessary for proper testing of the specimen.

Additional objects as well as features and advantages of this invention will become evident from the descriptions set forth hereinafter when considered in conjunction with the accompanying drawings.

BRIEF DESCRIPTION OF THE DRAWINGS

FIG. 1 is a perspective view of the invention in operation showing the control means which monitors the skin temperature of the form for the main structure and the temperature in one of the test molds. The control means compares the two temperature readings and adjusts the power to the heating units of the test mold accordingly so that the temperature of the concrete specimens in the molds matches that of the concrete in the main structure.

FIG. 2 is a perspective view of one of the molds showing the two halves of the mold that are pivotally mounted to each other to form an open-ended shape when the mold is closed and the insulated top member that can be placed over the open end of the mold shape. FIG. 2 also illustrates in a broken away section the protective cover that can be placed around the insulating material to protect it from wear and abuse.

FIG. 3 shows the mold halves in an open position in which the stop members positioned on the lower portions of each mold half abut each other to define a predetermined open position.

FIG. 4 shows the mold halves in their closed position with the heating units, insulation, and protective covers removed.

FIG. 5 is a view along line 5—5 of FIG. 4 illustrating the manner in which the securing members for selectively holding abutting pairs of flanges together are symmetrically positioned about the mold. Each securing means is positioned on one of the mold members as they extend in opposing directions so that they can be easily and quickly manipulated by one person.

FIG. 6 is a view of the mold showing the pivot arrangement and the overlapping, flexible sheet members that prevent material from falling through the crack between the mold halves as the mold is opened. These flexible sheet members protect the insulation that is positioned near the pivot means from wear and abuse.

FIG. 7 is a view along line 7—7 of FIG. 3 illustrating how the overlapping sheet members are flexed as the mold is opened. FIG. 7 also illustrates how the insulation material on the bottom of the mold has a flexible, compressible portion immediately adjacent the pivot means.

FIG. 8 is a view along line 8—8 of FIG. 1 showing a cross sectional view of one of the molds.

FIG. 9 illustrates a modification of the flexible sheet members positioned near the pivotal axis of the mold that prevent material from passing between the edges of the floor members of the mold halves as the mold is opened. In this modification, a single flexible sheet is supported by two guide members.

FIG. 10 is a view along line 10—10 of FIG. 9 illustrating the relationship between the flexible sheet and the guide members of the modification of FIG. 9.

FIG. 11 is a detailed view of the arrangement for aligning the mold halves as the mold closes. FIG. 11 also illustrates the manner in which a prying tool (shown in dotted lines) can be placed in the gap between the male and female members of the aligning arrangement to initially pry the mold halves apart.

FIG. 12 is a detailed view of the manner in which each securing member is pivotally mounted to a flange of a mold half.

FIG. 13 illustrates the stripping shoe that can be used to disengage a mold specimen that is sticking to one of the mold halves.

FIG. 14 shows the stripping shoe in use with the mold. When a test specimen sticks to one of the mold halves, the mold is moved to the open position and the stripping shoe is positioned adjacent the free mold half.

FIG. 15 is a view similar to FIG. 14 showing how the test specimen contacts the stripping shoe along an edge thereof and is disengaged from the one mold half. The stripping shoe contacts the test specimen interiorly of the edges and will disengage the test specimen from the mold without damaging the cylindrical boundary areas and their edges which are necessary for proper testing of the specimen.

DETAILED DESCRIPTION OF THE PREFERRED EMBODIMENT

As best seen in FIG. 1, one or more test molds 1 and 2 can be remotely positioned from form 3 of the much larger main structure with the temperature line 5 running from the form 3 and the temperature line 7 running from one or both of the test molds 1 and 2 to a control means 9. For purposes of illustration, the temperature of only one mold is shown as being monitored, however, each mold 1 and 2 can be individually monitored and supplied with electricity through its own power line. Each temperature line 5 and 7 is connected to a thermocouple or other temperature sensing device respectively positioned in or immediately adjacent the concrete of the material in the form 3 and the mold 1. The control means 9 compares the two temperature readings and selectively supplies electrical power through the power line 11 to heat the molds 1 and 2. In this manner, the time-temperature curve of the concrete curing in the form 3 is accurately followed and reproduced in the molds 1 and 2.

The electrically heated molds 1 and 2 have two substantially identical mold halves 17 and 19 that are pivotally mounted to each other adjacent one end portion as best seen in FIGS. 2, 3, and 6. In the closed position of FIGS. 2 and 4, the mold halves 17 and 19 abut each other along side flanges 21 to form an open-ended mold shape into which concrete can be poured. An insulated top member 23 can be placed over the open end of the mold shape and secured in place by a waterproof cap 25 as shown in FIGS. 1 and 8. The insulated top member 23 rests on top flanges 27 which extend outwardly from the curved wall member 29 of each mold half 17 and 19. If desired, the top member 23 can have a protective portion 24 made of steel or other material extending under it and up over two or more sides as shown in FIG. 2. The flanges 27 abut each other when the mold is closed and form a continuous planar surface that not only offers a large working surface but also protects other parts of the mold from wear and abuse.

As best seen in FIGS. 2, 3, and 11, a male member 31 is attached adjacent the surface of one flange 27 and protrudes beyond the bounds of the flange 27. The male member 31 is received in a recessed, open-sided female member 33 in the surface of the other flange 27 to align the mold halves 17 and 19 as the mold is closed. The female member 33 extends away from the edge 34 of the respective flange 27 in a first direction substantially perpendicular to the edge 34 and the open side of the female member 33 extends substantially in this first direction. Female member 33 also extends away from the edge 34 of the respective flange 27 for a greater distance than the male member 31 protrudes beyond the edge 34 of its flange 27 so that a gap 35 will exist between the two even when the mold is closed. As shown in FIG. 11, a prying tool 37 (shown in dotted lines) can be inserted through the open side of the recessed female member 33 into the gap 35 and twisted to initially pry the mold halves 17 and 19 apart.

The members for securing side flanges 21 of one mold half to the side flanges 21 of the other mold are best illustrated in FIGS. 3–5 and 12. Each securing means for holding an abutting pair of side flanges 21 together includes a threaded portion 39 that is pivotally mounted by a pivot pin 41 to a side flange 21 of each of the mold halves 17 and 19. Each securing means also includes a wing nut 43 and washer 45 positioned on the threaded portion 39. The threaded portions 39 are mounted to each respective mold half 17 and 19 approximately 180° from each other about the axis of the open-ended mold shape. In operation as seen in FIGS. 4 and 5, each threaded portion 39 can be moved about their pivotal axes with part thereof received in the respective open-ended slot 47 in side flanges 21. When in the securing position, the threaded portions 39 extend in opposite directions relative to their respective pivot pins 41 so that an operator can use both of his hands simultaneously to easily and quickly tighten the wing nuts 43 to secure a pair of abutting side flanges 21 together.

Referring to FIGS. 6 and 7, each bottom flange 49 of the mold has a floor portion 51 with a mold surface 53. The bottom flanges 49 are respectively attached to the wall members 29. Each mold surface 53 has a floor portion 51 which meets the mold surface 55 of a wall member 29 to form a continuous mold surface. As the mold is opened, the edges 57 of the floor portions 51 separate. To prevent any material from passing between the separated edges 57 and harming the flexible, insulation section 59 in FIG. 7, two flexible sheets 61 of spring steel are respectively mounted in an overlapping position by securing members 62 to the bottom flanges 49. The sheets 61 slide relative to each other and flex as the mold is opened. The flexible sheets 61 are positioned between two trios of knuckle supports 63 and 64 as best seen in FIG. 6. For ease of manufacture, each bottom flange 49 has a pair of spaced knuckles 63 on one side of the flexible sheets 61 and a single knuckle 64 on the other. The mold halves 17 and 19 can then be joined together with the single knuckle support 64 of one mold half inserted between the pair of knuckle supports 63 of the other half to form a trio. Once the knuckle supports 63 and 64 are aligned, pivot pins 65 can be inserted in each trio.

FIGS. 9 and 10 illustrate a modification of the means for preventing material from passing between the edges 57. In this embodiment, a single flexible sheet 67 of spring steel is secured at one side to one of the floor flanges 47. Guide members 69 and 71 are secured outwardly of the sheet 67 to each floor flange 49. The opposite side of the sheet 67 from the secured side is free to move between the guide members 71 and the respective floor flange 49 as the mold opens and closes. This sheet 67 like sheets 61 also flexes as the mold is opened. The sheet 67 and guide members 69 and 71 have end portions cut to extend along a knuckle support 63 at each trio in the direction of the pivotal axis of the mold as best seen in FIG. 9.

Each mold half 17 and 19 has stop members 73 with edges 75 as shown in FIGS. 2 and 3. Stop members 73 are symmetrically positioned on each mold half 17 and 19 and corresponding pairs of stop members 73 abut one another at a location along the edges 75 to define a predetermined open position for the mold. The edges 75 are substantially parallel to the edges 77 of the respective mold surface 55 of wall members 29 and, in one embodiment, stop members 73 are positioned so that the edges 75 of a pair of stop members 73 abut one another at an angle of about 45°. The flexible insulation portion 59 adjacent the stop members 73 flexes and compresses to accommodate the pivotal motion of the mold halves 17 and 19 as they are moved toward and away from the predetermined open position.

Referring to FIGS. 4 and 8, and electric heating unit 79 corresponding to the shape of the outer surface 81 of the wall member 29 is positioned immediately adjacent the surface 81. The power line 11 in FIGS. 1 and 2 runs to the plug 83 from which another line (not shown) delivers electricity to each heating unit 79. The wall member 29 has a passage 85 extending between its mold surface 55 and outer surface 81 as shown in FIG. 8. The thermocouple 86 and its lead line 88 are placed within the passage 85 with the thermocouple positioned substantially halfway up the wall member 29. The passage 85 can extend into the wall member 29 from above or below. If desired, the passage 85 can extend less than halfway into the wall member 29 as long as it is far enough away from flange 49 or 27 so the thermocouple 86 is not greatly affected by the gradient of the heat dissipating through these flanges. Each wall member 29 can have a passage 85 or, if desired, only one wall member 29 can have a passage 85. Rigid sections of insulation 87 are positioned about the heating units 79 and on either side of the flexible insulation section 59. Thin, protective covers 89 can be placed about the rigid insulation sections 87 to protect them from wear and abuse. Top flanges 27 and bottom flanges 49 extend outwardly of the mold to a point beyond the insulation section 87 and the protective covers 89 not only so that any excess heat within the mold can be passed outwardly therefrom through the flanges 27 and 49 but also to protect the insulation from damage. Should the mold be dropped on a surface, the flanges 29 and 49 will absorb the force rather than the weaker insulation.

The flanges 21, 27, and 49 as well as the wall members 29 can be made out of any material that will transfer heat. Preferably, these members are made from a metal that is easily casted, does not react with wet concrete, is lightweight, tough, hard, and easily machined. In one embodiment, these members are made out of a zinc alloy called "Korloy". The insulating material can also be made from any lightweight insulating materials and, in one embodiment, the rigid secitons of insulation are made from urethane foam and the flexible section 59 is made from compressible open-cell urethane foam.

FIGS. 14-15 show a stripping shoe 91 which is used to remove a molded test specimen that has become stuck or fixedly engaged with a mold surface of one of the mold halves 17 and 19. The stripping shoe 91 has an elongated first portion 93 and a second portion 95 attached thereto at approximately the same angle that the mold surfaces 53 and 55 meet each other. The first portion 93 and second portion 95 of the stripping shoe 91 can be slightly curved where they meet as shown in FIGS. 14 and 15 or can be joined at a right angle as shown in FIG. 13. The portions 93 and 95 of the stripping shoe 91 are substantially rectangular in cross section and a substantially rectangular contact member 97 is positioned on the second portion 95 of the stripping shoe 91 as best seen in FIG. 13. The contact member 97 is also substantially rectangular in cross section and, as illustrated in FIGS. 14 and 15, the stripping shoe can be inserted into the mold near one of the mold halves and the mold moved toward the closed position so that the edge 99 will initially contact the molded test specimen at a location interiorly of the test specimen and away from the boundary area 101 and its edges 103. Continued movement of the mold toward the closed position will disengage the molded test specimen from fixed engagement with the mold surface of the other mold half. In this manner, the molded test specimen is contacted by the stripping shoe in the boundary area corresponding to the mold surface 53 of the floor portion 51 and is removed from engagement with the one mold member without contacting the boundary area 101 and edges 103 which must remain intact for proper testing of the molded specimen.

The mold of this invention is primarily designed to make cylindrical test specimens of concrete, however, it works equally well with other materials. The heating units used in the preferred embodiment are relatively thin with a heating capacity of about 60 watts and it is contemplated that heating units with higher or lower capacity could be used. The shape of each heating unit is disclosed as conforming to the shape of the outer surface of each wall member but it is also contemplated that the shape of the heating units could vary.

While several embodiments of the present invention have been described in detail herein, various changes and modifications can be made without departing from the scope of the invention.

I claim:

1. A mold for making test specimens, said mold comprising:
two substantially identical mold members, each of said mold members having first and second end portions spaced from each other and a recessed mold surface with a first portion extending between said first and second end portions, each of said first portions of said mold surfaces having two substantially parallel edges extending in a direction between said first and second end portions of the respective mold member and defining boundaries of said first portion of each mold surface, said mold surface of each mold member further having a second portion connected to said first portion of said mold surface adjacent said first end portion of each mold member, each of said second portions of said mold surfaces having an edge extending between said two edges of the first portion of each respective mold surface and defining a boundary of said second portion of each mold surface,
means operably connected to each of said first end portions of said mold members for pivotally mounting said mold members to each other about a pivotal axis, said mold members being movable about said pivotal axis between a predetermined open position and a closed position, said edges of said first portion of the mold surface of one mold member and said edge of said second portion of the mold surface of said one mold member abutting the corresponding edges of the other mold member in said closed position to define an open-ended shape, and,
means for preventing movement of said mold members about said pivotal axis beyond said predetermined open position, said preventing means including a first pair of substantially identical stop members, each of said stop members being positioned on the first end portion of each respective mold member, said stop members being spaced from said pivotal axis and abutting each other at a first predetermined location as said mold members are moved about said pivotal axis away from said closed position to define said predetermined open position of said mold members.

2. The mold of claim 1 wherein each of said stop members has an edge, said stop members abutting each other at a location along each respective edge to define said predetermined open position of said mold members.

3. The mold of claim 2 wherein said preventing means includes a second pair of substantially identical stop members, each of said stop members of said second pair being positioned on said first end portion of said respective mold member at a location spaced from said first pair along said pivotal axis, said stop members of said second pair being spaced from said pivotal axis and abutting each other when said mold members are in said predetermined open position.

4. The mold of claim 3 wherein each of said second pair of stop members has an edge, said stop members abutting each other at a location along each respective edge when said mold members are in said predetermined open position.

5. The mold of claim 4 wherein the edges of each of said stop members on the respective mold members are substantially parallel to said edges of the first portion of said mold surface of said respective mold member.

6. The mold of claim 5 wherein said stop members of each pair abut each other with the edges thereof intersecting at approximately 45°.

7. The mold of claim 1 further including:
flexible compressible insulating foam and means for positioning said insulating foam adjacent said first end portions of said mold members, said insulating foam extending outwardly of said pivotal axis of said said mold members toward each of said first end portions, said insulating foam being compressed as said mold members are moved from said closed position toward said open position.

8. The mold of claim 7 wherein said insulating foam is open-cell urethane foam.

9. In a mold for making test specimens having two substantially identical mold members with recessed mold surfaces therein, said mold members being pivotally mounted to each other for movement between an open position and a closed position in which said mold members abut each other with the recessed mold surfaces forming an open-ended shape about an axis, each of said mold members further including at least two substantially planar flanges extending outwardly of each mold surface on opposite sides thereof, said flanges on one mold member abutting the corresponding flanges on the other mold member when said mold members are in the closed position, the improvement including:
means operably connectable between abutting flanges of the mold members for selectively securing said abutting flanges together, said securing means including two substantially identical securing members and means for mounting each of said securing members to one of each pair of abutting flanges, each of said two securing members being mounted to a different mold member at approximately 180° from the other about the axis of said open-ended shape formed by said mold members in said closed position whereby said mold members can be easily and quickly secured to each other by simultaneous manipulation of each of said securing means.

10. The improvement of claim 9 wherein each of said securing members has a first and second portion and each mounting means includes means for pivotally mounting said first portion of one of said securing members to said one flange of each abutting pair of flanges, each of the other flanges of each abutting pair having an open-ended slot for receiving part of said first portion of the respective securing member therein as said respective securing member is pivoted about the respective pivotal axis, said second portion of each of said securing members being movable relative to the first portion toward and away from the pivotal axis of said securing member whereby the first portion of each securing member can be pivoted to a position within the open-ended slot of the respective other flange and said second portion of said securing member moves toward the pivotal axis thereof to secure a respective pair of flanges in the abutting position.

11. The improvement of claim 10 wherein the first portion of each securing member has a threaded part and the second portion of each securing member is a threaded wingnut.

12. In a mold for making test specimens having two mold members with recessed mold surfaces therein, said mold members being pivotally mounted to each other for movement between an open position and a closed position in which said mold members abut each other with the recessed mold surfaces forming an open-ended shape, each of said mold members including a first member, each of said first members having an edge and a substantially planar surface, said edge and said surface being substantially parallel, said first members of the mold members abutting each other along said edges when said mold members are in said closed position with said surfaces of said first members forming a substantially continuous planar surface, the improvement including:
means for aligning said mold members as said mold members are moved toward a closed position, said aligning means including a male member, means to attach said male member adjacent the surface of one of said first members of said mold members with a portion of said male member protruding beyond said edge of said one first member, and, an open-sided female member positioned adjacent the surface of the other first member and recessed in said surface, said female member extending away from the edge of the other first member in a first direction, said open side of said female member extending substantially in said first direction, said female member substantially conforming to the shape of said male member for receiving said male member to align said mold members as said mold members are moved toward said closed position.

13. The improvement of claim 12 wherein said protruding portion of said male member extends beyond said edge of said one first member for a first distance and said recessed female member extending away from the edge of the other first member for a distance greater than said first distance whereby a gap is present between a portion of said female member and said protruding male member when said mold members are in the closed position so that a prying instrument could be inserted through said open side of said recessed female member into said gap to pry said mold members apart.

14. A mold for making test specimens, said mold comprising:
two mold members, each of said mold members having a recessed mold surface therein, means for pivotally mounting said mold members to each other for movement about a pivotal axis between an open position and a closed position, each of said mold surfaces having a first portion extending outwardly of said pivotal axis, each of said first portions having an edge spaced from and substantially parallel to said pivotal axis, said edges being substantially co-extensive and extending along said pivotal axis for a first fixed distance, said edges abutting each other when said mold members are in said closed position and being spaced from each other when said mold members are away from said closed position, said pivot means having a first portion and a second portion, said first and second portions being spaced from each other along said pivotal axis on either side beyond said first fixed distance of said edges, and,
means for substantially preventing passage of material between said edges of said mold surfaces as said mold members are moved away from said closed position.

15. The mold of claim 14 wherein said means for substantially preventing passage of material includes at least one flexible sheet member with two end portions and means to mount said at least one flexible sheet member adjacent said first portions of said molding surfaces with each end portion of said flexible sheet member spaced a greater distance from said pivotal axis and said edges of the mold surfaces.

16. The mold of claim 15 wherein said means for substantially preventing passage of material includes means for guiding the movement of said at least one flexible sheet member as said mold between said open and closed positions, said guiding means having two guide members and means for securing each guide member to a respective mold half, said at least one flexible sheet member having two boundary portions, said at least one flexible sheet being secured adjacent one of said boundary portions by said securing means of said guide means to one of said mold halves with said at least one flexible sheet member between each first portion of the mold half and the respective guide member with the other boundary portion free to move relative to the respective first portion and guide member secured thereto.

17. The mold of claim 16 wherein said guide members and said at least one flexible sheet member each have portions extending beyond said first fixed distance of the edges of said first portions.

18. The mold of claim 15 wherein said means for substantially preventing passage of material includes a second flexible sheet member with two end portions and means to mount said second flexible sheet member adjacent said first portion of said molding surfaces in an overlapping relationship with said first flexible sheet member, said second flexible sheet member being mounted with said end portions spaced a greater distance from said pivotal axis than said edges of the mold surfaces.

19. The mold of claim 18 wherein said flexible sheet members are made of spring steel.

20. The mold of claim 14 wherein said pivot means includes two pairs of knuckle supports and means to symmetrically mount each of said pairs to a different mold member on opposite sides of said first fixed distance of said edges, said pivot means further including two single knuckle supports and means to symmetrically mount each of said single knuckle supports to a different mold member on opposite sides of said first fixed distance of said edges, each knuckle support in said pairs of knuckle supports being spaced from the other knuckle support in said pair to receive one of said single knuckle supports therebetween to form a trio of knuckle supports, each of said knuckle supports having a hole therethrough and said pivot means further including two pivot pins each of which is receivable within the holes of a respective trio of knuckle supports.

21. The mold of claim 14 further including flexible, compressible insulating foam and means for positioning said insulating foam adjacent said means for substantially preventing passage of material whereby said insulating foam is compressed as said mold members are moved away from said closed position and said preventing means keeps any material in said mold from contacting said insulating foam.

22. The mold of claim 21 wherein said insulating foam is open-cell urethane foam.

23. An electrically heated mold for making test specimens of a material, said mold comprising:
two mold members, each of said mold members having a thin, heat transferring wall member with a mold surface and a second surface, means operably connected to said mold members for pivotally mounting said mold members to each other for movement about a pivotal axis, each of said wall members having at least two edges defining at least two boundaries of each respective mold surface, said mold members being movable about said pivotal axis between an open position and a closed position in which at least two edges of each mold surface abut two edges of the other mold surface to form a mold shape between said mold surfaces for receiving the material from which a test specimen is to be made,
electrical heating means, said electrical heating means having a heating unit substantially conforming to the shape of each of said second surfaces of said wall members for heating said thin, heat transferring wall members,
heat insulating material positioned about each of said heating units and extending away from each of said heating units for a first distance, and
each of said mold members having at least one heat transferring flange member attached to and extending away from said respective thin, heat transferring wall member of said mold members to a location beyond the outward extend of said heat insulating material, said heat transferring flange member passing some heat from each of said thin wall members outwardly of said mold.

24. An electrically heated mold for making test specimens of a material, said mold comprising:
two mold members, each of said mold members having a thin, heat transferring wall member with a mold surface and a second surface, means operably connected to said mold members for pivotally mounting said mold members to each other for movement about a pivotal axis, each of said wall members having at least two edges defining at least two boundaries of each respective mold surface, said mold members being movable about said pivotal axis between an open position and a closed position in which at least two edges of each mold surface abut two edges of the other mold surface to form a mold shape between said mold surfaces for receiving the material from which a test specimen is to be made, said mold surfaces forming a shape with one open end when said mold members are in said closed position, and,
electrical heating means, said electrical heating means having a heating unit substantially conforming to the shape of each of said second surfaces of said wall members for heating said thin, heat transferring wall members, said electrically heated mold further including insulating material positioned about said mold surfaces, said insulating material having a rigid portion substantially surrounding all of said mold surfaces and a flexible, compressible portion positioned adjacent said pivot means for accommodating the pivotal movement of said mold members.

25. The electrically heated mold of claim 24 further including an insulated top member positionable over the open end of the mold shape formed when said mold members are in said closed position.

26. The electrically heated mold of claim 25 further including at leaste one heat transferring flange member attached to each of said thin, heat-transferring wall members of said mold members and extending outwardly therefrom for a distance greater than the outward extent of said insulating material, said heat transferring flange members being substantially parallel to said pivotal axis and defining the open end of the mold shape when the mold members are in the closed position, said insulating top member being positionable upon said heat transferring flange members to cover the open end of said mold shape.

27. The electrically heated mold of claim 26 further including a substantially water tight cap positionable about said top member and the outward extent of said heat transferring flange members.

28. The electrically heated mold of claim 26 wherein each of said flange members has a substantially planar surface, said flange members abutting each other when said mold is in the closed position so that the respective surfaces of said flange members form a substantially continuous planar surface, said mold further including means for aligning said mold members as said mold members are moved toward said closed position, said aligning means including a male member, means to attach said male member adjacent the surface of one of said flange members with a portion of said male member protruding beyond the bounds of the surface of said one flange member, and, a female member positioned adjacent the surface of the other flange member and recessed in the surface thereof, said female member substantially conforming to the shape of said male member for receiving said male member to align said mold members as said mold members are moved toward said closed position.

29. The electrically heated mold of claim 28 wherein said protruding portion of said male member extends beyond the bounds of the surface of said one flange member for a first distance and said recessed female member extends away from the bounds of the surface of the other flange member for a distance greater than said first distance whereby a gap is present between a portion of said female member and said protruding male member when said mold members are in the closed position so that a prying instrument could be inserted into said gap to pry said mold members apart.

30. The electrically heated mold of claim 29 further including stop members symmetrically positioned on each mold member, said stop members on each mold member abutting corresponding stop members on the other mold member as said mold is opened to define said open position of the mold members.

31. The electrically heated mold of claim 29 further including:
at least two flange members attached to and extending outwardly of each mold surface of the respective wall members, said flange members on one mold member abutting corresponding flanges on the other mold member when said mold members are in the closed position, and,
means operably connectable between abutting flanges of the mold members for selectively securing said abutting flanges together, said securing means including two substantially identical securing members and means for mounting each of said securing members to one of each pair of abutting flanges, each of said two securing members being mounted to a different mold member at approximately 180° from the other about an axis whereby said mold members can be easily and quickly secured to each other by simultaneous manipulation of each of said securing means.

32. The electrically heated mold of claim 31 wherein said mounting means for each of said securing members includes a pivot pin for pivotally mounting each of said securing members to one of each pair of abutting flanges, each of said securing members having a threaded portion extending outwardly of the respective pivot pin, said securing means further including two threaded wing nuts and the other abutting flange of each pair further including an open-ended slot for selectively receiving part of the respective securing member whereby each of said securing members can be pivoted about the respective pivot pin to a position with said part thereof received in the respective open-ended slot of the respective other abutting flange of each pair and each of said threaded wing nuts respectively tightened on the threaded portion of one of the securing members to secure the respective abutting pair of flanges together, said securing members extending outwardly of the respective pivot pins in opposite directions from each other when said respective pairs of abutting flanges are secured together.

33. The electrically heated mold of claim 24 wherein said mold surface of each mold member has a third edge adjacent said pivot means and extending substantially parallel to said pivotal axis, said third edges abutting each other when said mold members are in said closed position and being spaced from each other when said mold members are moved away from said closed position, said electrically heated mold further including means for substantially preventing passage of material between said third edges as said mold members are moved away from the closed position, said preventing means including at least one flexible sheet member and means for securing said at least one flexible sheet member adjacent said pivot means between said flexible, compressible portion of said insulating material and said third edges.

34. An electrically heated mold for making test specimens of a material, said mold comprising:
two mold members, each of said mold members having a thin, heat transferring wall member with a mold surface and a second surface, means operably connected to said mold members for pivotally mounting said mold members to each other for movement about a pivotal axis, each of said wall members having at least two edges defining at least two boundaries of each respective mold surface, said mold members being movable about said pivotal axis between an open position and a closed position in which at least two edges of each mold surface abut two edges of the other mold surface to form a mold shape between said mold surfaces for receiving the material from which a test specimen is to be made, each of said mold members further having a floor member with a mold surface, each of said floor members being attached to a respective wall member with the wall and floor mold surfaces meeting at an angle,
electrical heating means, said electrical heating means having a heating unit substantially conforming to the shape of each of said second surfaces of said wall members for heating said thin, heat transferring wall members and,
an elongated stripping shoe having a first portion and a second portion, said first and second portions being joined at an angle substantially equal to the angle between the mold surfaces of the floor member and wall member of each mold member whereby said mold members can be moved to said open position if said mold specimen is fixedly engaged with one of said mold members and said stripping shoe inserted in the other of said mold members with a first portion of said stripping shoe resting on said mold surface of said floor member of said other mold member so that said molded specimen will be contacted by said first portion of said stripping shoe and disengaged from said one mold member as said mold members are moved toward said closed position.

* * * * *